US008273708B2

(12) United States Patent
Bueno et al.

(10) Patent No.: US 8,273,708 B2
(45) Date of Patent: Sep. 25, 2012

(54) METHODS OF TREATMENT OF OCULAR SURFACE PATHOLOGIES

(76) Inventors: Lionel Bueno, Aussonne (FR); Marie-Thérése Droy-Lefaix, Hermes (FR); Philippe Caron, Vence (FR)

(*) Notice: Subject to any disclaimer, the term of this patent is extended or adjusted under 35 U.S.C. 154(b) by 405 days.

(21) Appl. No.: 11/792,290

(22) PCT Filed: Dec. 9, 2005

(86) PCT No.: PCT/FR2005/003095
§ 371 (c)(1),
(2), (4) Date: Jun. 28, 2007

(87) PCT Pub. No.: WO2006/061525
PCT Pub. Date: Jun. 15, 2006

(65) Prior Publication Data
US 2008/0139451 A1   Jun. 12, 2008

(30) Foreign Application Priority Data
Dec. 9, 2004  (FR) .................................. 04 13136

(51) Int. Cl.
*A61K 38/00* (2006.01)
*A61K 31/67* (2006.01)
*A61K 47/06* (2006.01)
*C12P 15/00* (2006.01)
*C12P 13/00* (2006.01)
*C12P 7/00* (2006.01)
(52) U.S. Cl. ............ 514/1.3; 514/95; 435/127; 435/132
(58) Field of Classification Search ........................ None
See application file for complete search history.

(56) References Cited

U.S. PATENT DOCUMENTS

| 5,030,631 | A | 7/1991 | Bauer |
| 5,189,056 | A | 2/1993 | Orlando et al. |
| 5,336,503 | A | 8/1994 | Wakasugi |
| 5,883,114 | A | 3/1999 | Kleinschroth |
| 6,248,549 | B1 | 6/2001 | Van Eyk et al. |
| 6,696,480 | B2 | 2/2004 | Liao |
| 7,452,877 | B2 | 11/2008 | Bueno |
| 2002/0045564 | A1 | 4/2002 | Van Eyk et al. |
| 2002/0091082 | A1 | 7/2002 | Aiello |
| 2005/0019314 | A1 | 1/2005 | Bueno |

FOREIGN PATENT DOCUMENTS

| EP | 0 638 564 | 2/1995 |
| EP | 0 797 992 | 10/1997 |
| EP | 0 797 992 A2 | 10/1997 |
| EP | 0 956 865 A1 | 11/1999 |
| EP | 1 417 976 | 5/2004 |
| FR | 2 674 434 | 10/1992 |
| RU | 2 148 997 | 5/2000 |
| WO | 97/30701 | 8/1997 |
| WO | WO 98/14186 | 4/1998 |
| WO | WO 98/37096 | 8/1998 |
| WO | WO 99/14242 | 3/1999 |
| WO | WO 00/03746 | 1/2000 |
| WO | WO 00/07609 | 2/2000 |
| WO | WO 00/57727 | 10/2000 |
| WO | WO 02/14499 | 2/2002 |
| WO | WO 02/058687 | 8/2002 |
| WO | 2005/112918 | 12/2005 |

OTHER PUBLICATIONS

Burgess et al. J of Cell Bio. 1990, 111:2129-2138.*
Pawson et al. 2003, Science 300:445-452.*
International Search Report for PCT/FR2005/003095 mailed Nov. 24, 2006 (English and French).
Database Biosis [Online], Biosciences Information Service, Satpathy et al., "Thrombin—Induced Inter—Endothelial Gap Formation in Bovine Corneal Endothelial Cells," 2003, data base accession No. PREV200300551552, abstract, XP002338320, 1 page.
Oikawa et al., "Potent inhibition of angiogenesis by wortmannin, a fungal metabolite," European Journal of Pharmacology, vol. 318, 1996, pp. 93-96, XP002906145.
Honjo et al., "A Myosin Light Chain Kinase Inhibitor, ML-9, Lowers the Intraocular Pressure in Rabbit Eyes," Experimental Eye Research, vol. 75, No. 2, Aug. 2002, pp. 135-142, XP008050231.
Wang et al., "Activation of ERK1/2 MAP kinase pathway induces tight junction disruption in human corneal epithelial cells," Experimental Eye Research, Jan. 2004, vol. 78, No. 1, pp. 125-136, XP008050258.
Rojanasakul et al., "The cytoskeleton of the cornea and its role in tight junction permeability," International Journal of Pharmaceutics, vol. 68, No. 1-3, 1991, pp. 135-149, XP008050244.
Wilson et al, "$Ca^{2+}$ Activation of Smooth Muscle Contraction", The Journal of Biological Chemistry, vol. 277, No. 3, pp. 2186-2192, 2002.
Williams et al, "Quantification of ocular inflammation: evaluation of polymorphonuclear leucocyte infiltration by measuring myeloperoxidase activity", Curr Eye Res. 1982-1983;2(7):465-70.

(Continued)

*Primary Examiner* — Chang-Yu Wang
(74) *Attorney, Agent, or Firm* — Nixon & Vanderhye P.C.

(57) ABSTRACT

The invention concerns compositions and methods for treating and/or preventing ocular pathologies. The invention also concerns compositions and methods enabling the regulation of paracellular permeability of the ocular epithelium. The compositions and methods of the invention are based in particular on the use of agents or conditions modulating the opening of tight junctions of the ocular epithelium. The invention can be used for preventive or curative treatment of various pathologies, such as pathologies of the ocular surface in mammals, particularly in human beings.

7 Claims, 6 Drawing Sheets

OTHER PUBLICATIONS

Figure 1:
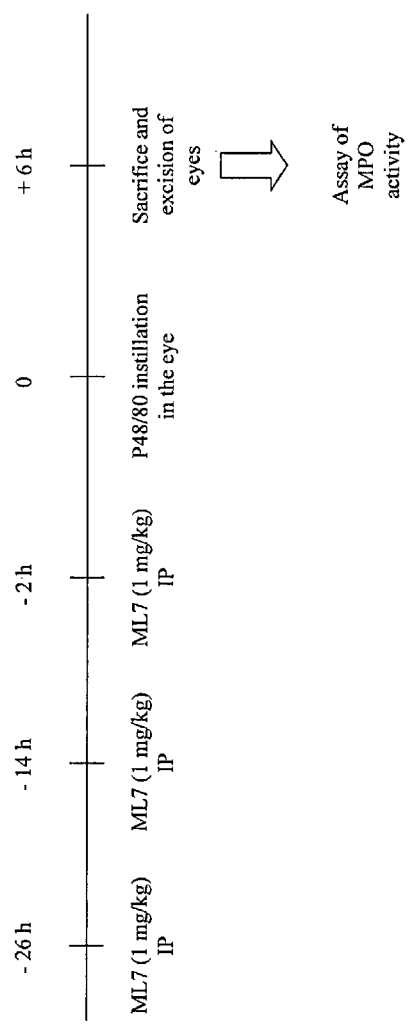

Bucolo et al, "Effects of Mipragoside® on Ocular Allergic Inflammation in the Rabbit", Journal of Ocular Pharmacology, vol. 9, No. 4, pp. 321-332, 1993.

Allansmith et al, "Ocular anaphylaxis induced in the rat by topical application of compound 48/80 dose response and time course study", ACTA Ophthalmologica 67, Supplementum 192, 145-153, (1989).

Pearlman et al, "The Role of Eosinophils and Neutrophils in Helminth-Induced Keratitis", Invest Ophthalmol Vis Sci 1998;39:1176-1182.

Takano et al, "Inflammatory cells in brush cytology samples correlate with the severity of corneal lesions in atopic keratoconjunctivitis", Br J Ophthalmol 2004;88:1504-1505.

Ma et al, "Cytochalasin B Modulation of Caco-2 Tight Junction Barrier: Role of Myosin Light Chain Kinase", American Journal of Physiology: Gastrointestinal and Liver Physiology, American Physiological Society, US, vol. 279, No. 5, Nov. 2000, pp. G875-G885.

Ma et al, "Mechanism of Extracellular Calcium Regulation of Intestinal Epithelial Tight Junction Permeability: Role of Cytoskeletal Involvement", Microscopy Research and Technique, Wiley-Liss, Chichester, GB, vol. 51, No. 2, Oct. 15, 2000, pp. 156-168.

Database Medline: US National Library of Medicine (NLM), Bethesda, MD, US; Jun. 2000 Mankertz et al, "Expression from the human occludin promoter is affected by tumor necrosis factor alpha and interferon gamma" & Journal of Cell Science, England, Jun. 2000, vol. 113, (Pt 11), Jun. 2000, pp. 2085-2090.

Banan et al, "Carbonylation and Disassembly of the F-Actin Cytoskeletin in Oxidant Induced Barrier Dysfunction and Its Prevention by Epidermal Growth Factor and Transforming Growth Factor Alpha in a Human Colonic Cell Line", Gut, British Medical Association, London, GB, vol. 46, No. 6, Jun. 2000, pp. 830-837.

Turner, "'Putting on the Squeeze' on the tight Junction: Understanding Cytoskeletal Regulation", Seminars in Cell and Developmental Biology, Academic Press, GB, vol. 11, No. 4, Aug. 2000, pp. 301-308.

Walsh et al, "Hepatocyte Growth Factor Influences Tight Junctions Via Regulation of the Apical Perijunctional Actin Cytoskeleten", Gastroenterology, W.B. Saunders Company, Philadelphia, US, vol. 118, No. 4, SUPPL 2PT, Apr. 2000, pp. AGA-A671.

Sims et al, "Inhibitors of Myosin Light Chain Kinase Modulate Tight Junctions in CACO-2 Cells", Journal of Physiology, vol. 493P, 1996, pp. 87P-88P.

Turner et al, "Physiological Regulation of Epithelial Tight Junctions is Associated With Myosin Light-chain Phosphorylation", American Journal of Physiology, American Physiological Society, Bethesda, MD, US, vol. 273, No. 4, Part 1, Oct. 1997, pp. C1378-C1385.

Ma et al, "Ethanol Modulation of Intestin Epithelial Tight Junction Barrier", American Journal of Physiology, American Physiological Society, Bethesda MD, US, vol. 276, No. 4, Part1, Apr. 1999, pp. G965-G974.

Heyman et al, "Cytokine-Induced Alteration of the Epithelial Barrier to Food Antigens in Disease", Annals of the New York Academy of Sciences, New York Academy of Sciences, New York, NY, US, vol. 915, 2000, pp. 304-311.

Gassier et al, "Inflammatory Bowel Disease is Associated with Changes of Enterocytic Junctions", American Journal of Physiology: Gastrointestinal and Liver Physiology, American Physiological Society, US, vol. 281, No. 1, Jul. 2001, pp. G216-G228.

Kucharzik et al, "Neutrophil Transmigration in Inflammatory Bowel Disease is Associated with Differential Expression of Epithelial Intercellular Junction Proteins", American Journal of Pathology, Philadelphia, PA, US, vol. 159, No. 6, Dec. 2001, pp. 2001-2009.

Database Medline, US National Library of Medicine (NLM), Bethesda, MD, US; Feb. 2002, Cho So Yean et al, "Enhancement of paracellular transport of heparin disaccharide across Caco-2 cell monolayers", & Archives of Pharmacal Research, Korea (South), Feb. 2002, vol. 25, No. 1, Feb. 2002, pp. 86-92.

Mi Won Son et al, "Protective Effect of Taurine on TNBS-Induced Inflammatory Bowel Disease in Rats", Archives of Pharmacal Research, Natl. Fisheries University, Pusan, KR, vol. 21, No. 5, Oct. 1998, pp. 531-536.

Simonovic et al, "Enteropathogenic *Escherichia coli* Dephosphorylates and Dissociates Eccludin from Intestinal Epithelial Tight Junctions", Cellular Microbiology, Blackwell Science, Oxford, GB, vol. 2, No. 4, Aug. 2000, pp. 305-315.

Simmons et al, "Bidirectional Sodium Ion Movement via the Paracellular and Transcellular Routes Across Short-Circuited Rabbit Ileum", Biochimica Et Biophysica Acta, Amsterdam, NL, vol. 448, No. 3, 1976, pp. 426-450.

Fasano et al, "Zonula Occludens Toxin Modulates tight Junctions Through Protein Kinase C-Dependent Actin Reorganization, in Vitro", Journal of Clinical Investigation, New York, NY, US, vol. 96, Aug. 1, 1995, pp. 710-720.

Karayiannakis et al, "Expression of Catenins and E-Cadherin During Epithelial Restitution in Inflammatory Bowel Disease", Journal of Pathology, Chichester, Sussex, GB, vol. 185, No. 4, Aug. 1998, pp. 413-418.

Soderholm et al, "Augmented Increase in Tight Junction Permeability by Luminal Stimuli in the Non-Inflamed Ileum of Crohn's Disease", GUT, British Medical Association, London, GB, vol. 50, No. 3, Mar. 2002, pp. 307-313.

Perry et al, "Reduced Cadherin-Catenin Complex Expression in Celiac Disease Can Be Reproduced in Vitro by Cytokine Stimulation", Laboratory Investigation, United States and Canadian Academy of Pathology, Baltimore, US, vol. 79, No. 12, Dec. 1999, pp. 1489-1499.

Patent Abstracts of Japan vol. 1998, No. 01, Jan. 30, 1998 & JP 09 241177, Sep. 16, 1997.

Groot, "Correlation Between Electrophysiological Phenomena and Transport of Macromolecules in Intestinal Epithelium", Veterinary Quarterly, Kluwer, Dordrecht, NL, vol. 20, no. Suppl 3, Jun. 1998, pp. S45-S49.

Savkovic et al, "EPEC-Activated ERK1/2 Participate in Inflammatory Response BT Not Tight Junction Barrier Disruption", American Journal of Physiology: Gastrointestinal and Liver Physiology, American Physiological Society, US, vol. 281, No. 4, Oct. 2001, pp. G890-G898.

Fasano et al, "Zonulin, a newly discovered modulator of intestinal permeability, and its expression in coeliac disease", LANCET, vol. 355, No. 9214, Apr. 29, 2000, pp. 1518-1519.

Kiliaan et al, "Stress stimulates transepithelial macromolecular uptake in rat jejunum" American Journal of Physiology 1998 United States, vol. 275, No. 5, 38-5, 1998, pp. G1037-G1044.

Verhaeren et al, "The Effect of 2,4,6-Triaminopyrimidine on Increased Mucosal Permeability of Guinea-Pig Colonic Mucosa, Following Administration of 1,8-Dihydroxy-Anthraquinonem, Salicylic Acid and Dinitrophenol", Pharmaceutisch Weekblad Scientific Edition, Bohn, Scheltema and Holkema, Amsterdam, NL, vo. 3, No. 1, Feb. 20, 1981, pp. 815-819.

Database Biosis, Biosciences Information Service, Philadelphia, PA, US; 1990, Gato-Pecina et al, "Use of the Paracellular Way for the Intestinal Absorption of Sugars" & Revista Espanola De Fisiologia, vol. 46, No. 4, 1990, pp. 343-352.

Krejs et al, "Effect of Protonated 2,4,6-Triaminopyrimidine, a Tight Junction Blocker, on Intestinal Transport in Dog Ileum in Vivo", Gastroenterology, Saunders, Philadelphia, PA, U, vol. 72, No. 4, Part 1, 1977, pp. 685-691.

Kinugasa et al, "Clauding Regulate the Intestinal Barrier in Response to Immune Mediators", Gastroenterology, W.B. Saunders Company, Philadelphia, US, vol. 118, No. 6, Jun. 2000, pp. 1001-1011.

Pothoulakis, "Effects of Clostridium Difficile Toxins on Epithelial Cell Barrier", Annals of the New Academy of Sciences, New York Academy of Sciences, New York, NY, US, vol. 915, 2000, pp. 347-356.

Hollander, "Intestinal Permeability, Leaky Gut, and Intestinal Disorders", Current Gastroenterology Reports, Current Science, US, vol. 1, No. 5, Oct. 1999.

Perry et al, "Intestinal permeability in coeliac disease", LANCET, vol. 358, No. 9294, Nov. 17, 2001, pp. 1729-1730.

Perry et al, "Reduced Expression of Z0-1 and Gamma Catenin in the Small Intestinal Mucosa of Untreated Cellac Disease", Gastroenterology, W.B. Saunders Company, Philadelphia, US, vol. 118, No. 4, Apr. 2000, p. AGAA369.

Choon Jin Ooi et al, "Regulation of Tight Junction Proteins in Human Subjects with Inflammatory Bowel Disease" Gastroenterology, W.B. Saunders Company, Philadelphia, Us, vol. 118, No. 4, Apr. 2000, pp. AGAA795.

Ferrier et al, "Stress-Induced Disruption of Colonic Epithelial Barrier: Role of Interferon-γ and Myosin Light Chain Kinase in Mice", Gastroenterology 2003; 125:795-804.

Cenac et al, "PAR$_2$ activation alters colonic paracellular permeability in mice via IFN-γ-dependent and -independent pathways", J. Physiol. 558.3 (2004), pp. 913-925.

Ait-Belgnaoui et al, "Acute Stress-induced hypersensitivity to colonic distension depends upon increase in paracellular permeability: role of myosin light chain kinase", Pain 113 (2005) 141-147.

Camilleri et al, "Intestinal Permeability and irritable bowel syndrome", Neurogastroenterology and Motility (2007), pp. 1-8.

Cenac et al, "Proteinase-Activated Receptor-2-Induced Colonic Inflammation in Mice: Possible Involvement of Afferent Neurons, Nitric Oxide, and Paracellular Permeability", The Journal of Immunology, 2003, 170:4296-4300.

Moriez et al, "Myosin Light Chain Kinase Is Involved in Lipopolysaccharide-Induced Disruption of Colonic Epithelial Barrier and Bacterial Translocation in Rats", American Journal of Pathology, vol. 167, No. 4, Oct. 2005, pp. 1071-1079.

Declaration Under Rule 132 of Lionel Bueno, Ph.D. executed Aug. 16, 2007 with professional resume.

Bradesi et al, "Acute and chronic stress differently affect visceral sensitivity to rectal distension in female rats", Neurogastroenterol. Mot. (2002) 14, 75-82.

Toulouse et al, "Role of tachykinin NK$_2$ receptors in normal and altered rectal senstiv", British Journal of Pharmacology (2000) 129, 193-199.

Maruoka et al, "Involvement of Rho and Myosin Light Chain Kinase in neutrophil elastase-induced morphological changes in airway epithelial cells", Am. J. Respir. Critical Care Med., vol. 159, No. 3suppl, 1999, p. a187.

Garcia et al, "Regulation of endothelial cell myosin light chain kinase by Rho. Cortactin, and p60(src)", The American Journal of Physiology, vol. 276, No. 6 pt 1, Jun. 1999, pp. L-989-L-998.

Parker, "Inhibitors of myosin light chain kinase and phosphodiesterase reduce ventilator-induced lung injury", Journal of Applied Physiology, vol. 89, No. 6, Dec. 2000, pp. 2241-2248.

Garcia et al, "Adherent neutrophils activate endothelial myosin light chain kinase: role in transendothelial migration", Journal of Applied Physiology, vol. 84, No. 5, May 1998, pp. 1817-1821.

Wyatt et al, "Stimulation of protein kinase C activity by tumor necrosis factor-α in bovine bronchial epithelial cells", American Journal of Physiology—Lung Cellular and Molecular Physiology, vol. 273, No. 5 17-5, 1997, pp. L1007-L1012.

Volberg et al, "Effect of protein kinase inhibitor H-7 on the contractility, integrity, and membrane anchorage of the microfilament system", Cell Motility and the Cytoskeleton, vol. 29, No. 4, 1994, pp. 321-338.

Kobayashi et al, "Mechanism of Hydrogen Peroxide-induced Inhibition of Sheep Airway Cilia", American Journal of Respiratory Cell and Molecular Biology, vol. 6, No. 6, 1992, pp. 667-673.

Xueliang et al, "Myosin Light Chain Phosphatase Activity in Ragweed Pollen-Sensitized Canine Traceal Smooth Muscle", American Journal of Respiratory Cell and Molecular Biology, vol. 11, No. 6, 1994, pp. 676-681.

Leff, "Pharmacologic management of asthma", Journal of Allergy and Clinical Immunology, vol. 101, No. 2 II, 1998, pp. S397-S399.

Ahdieh et al, "Lung epithelial barrier function and wound healing are decreased by IL-4 and IL-13 and enhanced by IFN-y" American Journal of Physiology, Cell Physiology, American Physiological Society, vol. 281, No. 6, Dec. 2001, pp. C2029-C2038.

Godfrey, "Human Airway Epithelial Tight Junctions", Microscopy Research and Technique, Wiley-Liss, Chichester, GB, vol. 38, No. 5, Sep. 1, 1997, pp. 488-499.

Kobayashi et al, "Immunohistochemical Study of E-cadherin and ZO-1 in Allergic Nasal Epithelium of the Guinea Pig", International Archives of Allergy and Immunology, vol. 116, No. 3, Jul. 1998, pp. 196-205.

Ohashi et al, "Relationship between bronchial reactivity to inhaled acetylcholine eosinophil infiltration and a widening of the intercellular space in patients with asthma", ARERUGI= Alergy. Japan, vol. 39, No. 11, Nov. 1990, pp. 1541-1545.

Citi et al, "Cytoskeletal involvement in the modulation of cell-cell junctions by protein kinase inhibitor H-7", Journal of Cell Science, vol. 107, No. 3, 1994, pp. 683-692.

Citi, "Protein Kinase Inhibitors Prevent Junction Dissociation Induced by Low Extracellular Calcium in MDCK Epithelial Cells", Journal of Cell Biology, vol. 117, No. 1, Apr. 1992, pp. 169-178.

Petrache et al, "Differential effect of MLC kinase in TNF-α-induced endothelial cell apoptosis and barrier dysfunction", American Journal of Physiology. Lung Cellular and Molecular Physiology, vol. 280. No. 6, Jun. 2001, pp. L1168-L1178.

Tamaoki, "Molecular mechanisms of airway epithelial cell remodeling in asthma", Recent Research Developments in Allergy & Clinical Immunology, 1 (2000), pp. 1-10.

Hashimoto et al, "Mitogen-activated protein kinase involves neutrophil elastase-induced morphological changes in human bronchial epithelial cells", Life Sciences, vol. 64, No. 16 (1999), pp. 1465-1471.

Fleisz ig et al, "Evidence for SRC-family tyrosine kinase and MAP kinase activity in Pseudomonas aeruginosa host cell invasion", XP-008011509, IOVS, vol. 40, No. 4 (Mar. 15, 1999), pp. S793.

Tsang et al, "Inhibitors of tyrosine kinase signaling cascade attenuated antigen challenge of guinea-pig airways in vitro", Am. J. Respir. Crit. Care Med., vol. 162 (2000), pp. 126-133.

Kempen et al, "Eotaxin induces degranulation and chemotaxis of eosinophils through the activation of ERK2 and p38 mitogen-activated protein kinases", Blood, vol. 95 No. 6 (Mar. 15, 2000), pp. 1911-1917.

Gesck et al, "Stimulates Na Absorption in CF Airway Cells Through Translation and MAPK-dependent Patways", XP008011050, Experimental Biology, vol. 16, No. 5 (Mar. 22, 2002), pp. A1146.

Liaw et al, "Effect of in vitro and in vivo aerosolized treatment with geniposide on tracheal permeability in ovalbumin-induced guinea pigs", European Journal of Pharmacology vol. 433, No. 1 (2001), pp. 115-121.

Schneeberger et al, "Structure, function and regulation of cellular tight junctions", The American Physiological Society, vol. 262, No. 6, Part 1 (Jun. 1992), pp. L647-L661.

Gordon et al, "Taurine Protects Hamster Bronchioles From Acute NO$_2$-Induced Alterations", The American Journal of Pathology, vol. 125, No. 3 (Dec. 1986), pp. 585-600.

Gordon et al, "Membrane Perturbations and Mediation of Gap Junction Formation in Response to Taurine Treatment in Normal and Injured Alveolar Epithelia", Experimental Lung Research, vol. 15, No. 6 (Dec. 1989), pp. 895-908.

Gordon et al, "Taurine Protects Rat Bronchioles from Acute Ozone Exposure: A Freeze Fracture and Electron Microscopic Study", Experimental Lung Research, vol. 24, No. 5 (Sep. 1998), pp. 659-674.

Ahdieh et al, "Lung epithelial barrier function and wound healing are decreased by IL-4 and IL-13 and enhanced by IFN-gamma", Am. J. Physiol. Cell Physiol, vol. 281, No. 6 (Dec. 2001), pp. C2029-C2038.

Godfrey, "Human Airway Epithelial Tight Junctions", Microscopy Research and Technique, vol. 38, No. 5 (Sep. 1, 1997), pp. 488-499.

Winton et al, "Class specific inhibition of house dust mite proteinases which cleave cell adhesion, induce cell death and which increase the permeability of lung epithelium", British Journal of Pharmacology, vol. 124, No. 6 (Jul. 1998), pp. 1048-1059.

Stevenson, "Understanding tight junction clinical physiology at the molecular level", The Journal of Clinical Investigation, vol. 104, No. 1 (Jul. 1999), pp. 3-4.

Cavanaugh et al, "Role of Stretch on Tight Junction Structure in Alveolar Epithelial Cells", American Journal of Respiratory Cell and Molecular Biology, vol. 25, No. 5 (Nov. 2001), pp. 584-591.

Bhat et al, "Regulation of Tight Junction Permeability by Calcium Mediators and Cell Cytoskeleton in Rabbit Tracheal Epithelium", Pharmaceutical Research, vol. 10, No. 7 (Jul. 1993), pp. 991-997.

Turner, "'Putting the squeeze' on the tight junction: understanding cytoskeletal regulation", Cell & Seminars in Cells & Developmental Biology, vol. 11, No. 4 (Aug. 2000), pp. 301-308.

Bhalla et al, "Airway Permeability in Rats Exposed to Ozone or Treated with Cytoskeleton-Destabilizing Drugs", Experimental Lung Research, vol. 14, No. 4 (1988), pp. 501-525.

Carayol et al, "Modulation of Cadherin and Catenins Expression by Tumor Necrosis Factor-α and Dexamethasone in Human Bronchial Epithelial Cells", American Journal of Respiratory Cell and Molecular Biology, vol. 26, No. 3 (Mar. 2002), pp. 341-347.

Takeuchi et al, "Histamine alters gene expression in cultured human nasal epithelial", The Journal of Allergy and Clinical Immunology, vol. 107, No. 2 (Feb. 2001), pp. 310-314.

Ohashi et al, "Relationship between bronchial reactivity to inhaled acetylcholine, eosinophil infiltration and a widening of the intercellular space in patients with asthma", Arerugi = [Allergy], Japan, vol. 39, No. 11 (Nov. 1990), pp. 1541-1545.

Cortijo et al, "Effects of taurine on pulmonary responses to antigen in sensitized Brown-Norway rats", European Journal of Pharmacology, vol. 431, No. 1 (Nov. 9, 2001), pp. 111-117.

Boehme et al, "Activation of Mitogen-Activated Protein Kinase Regulates Eotaxin-Induced Eosinophil Migration", The Journal of Immunology, vol. 163 (Aug. 1, 1999), pp. 1611-1618.

Petrache et al, "The role of the microfilament cytoskeleton in TNF—α-induced pulmonary endothelial cell barrier dysfunction", Federation of American Societies for Experimental Biology, vol. 15, No. 4 (Mar. 31, 2001), pp. A163.

Jiang et al, "Ragweed Sensitization-induced Increase of Myosin Light Chain Kinase Content in Canine Airway Smooth Muscle", Am. J. Respir. Cell Mol. Biol., vol. 7, pp. 567-573, 1992.

Eutamene et al, "LPS-induced lung inflammation is linked to increased epithelial permeability: role of MLCK", European Respiratory Journal, vol. 25, No. 5, 789-796, 2005.

Youakim et al, "Interferon-γ decreases barrier function in T84 cells by reducing ZO-1 levels and disrupting apical actin", Am J Physiol Gastrointest Liver Physiol 276:1279-1288, 1999.

Ahdieh et al, "Lung epithelial barrier function and wound healing are decreased by IL-4 and IL-13 and enhanced by IFN-gamma", Am J Physiol Cell Physiol 281:2029-2038, 2001.

Heyworth et al, "Naphthalenesulfonamides block neutrophil superoxide production by intact cells and in a cell-free system: is myosin light chain kinase responsible for these effects?", Biochemical Journal (1995) 311(1), 81-7 (Abstract).

Kelley et al, "Candidate inhibitor of the volume-sensitive kinase regulating K-Cl cotransport: the myosin light chain kinase inhibitor ML-7", Journal of Membrane Biology (2000), 178(1), 31-41 (Abstract).

Schmidt et al, "Molecular mechanisms in allergy and clinical immunology", J. Allergy Clin. Immunol, Apr. 2000, pp. 673-682.

Parker, "Inhibitors of myosin light chain kinase and phosphodiesterase reduce ventilator-induced lung injury", J Appl Physiol 2000, vol. 89, pp. 2241-2248.

Rabe et al, "Pharmacological treatment of asthma today", Eur. Respir. J., Jul. 2001, vol. 18 (suppl. 34), pp. 34s-40s.

Wan et al, "Der p 1 facilitates transepithelial allergen delivery by disruption of tight junctions", Journal of Clinical Investigation, Jul. 1999, vol. 104, issue 1, pp. 123-133.

Tinsley et al, "Myosin light chain kinase transference induces myosin light chain activation and endothelial hyperpermeability", Am J Physiol Cell Physiol 2000, vol. 279, pp. C1285-C1289/.

Turner et al, "Physiological regulation of epithelial tight junctions is associated with myosin light-chain phosphorylation", American Journal of Physiology-Cell Physiology; 1997, vol. 273, No. 4; pp. C1378-1385.

Dudek et al, "Cytoskeletal regulation of pulmonary vascular permeability", J Appl Physiol, 2001, vol. 91, pp. 1487-1500.

Ma et al, "Cytochalasin B modulation of Caco-2 tight junction barrier: role of myosin light chain kinase" Am J Physiol. Gastrointest. Liver Physiol., 2000, vol. 279, pp. G875-G885.

Bhat et al, "Regulation of Tight Junction Permeability by Calcium Mediators and Cell Cytoskeleton in Rabbit Tracheal Epithelium", Pharmaceutical Research, 1993, vol. 10, No. 7, pp. 991-997.

* cited by examiner

METHODS OF TREATMENT OF OCULAR SURFACE PATHOLOGIES

This application is the US national phase of international application PCT/FR2005/003095 filed 9 Dec. 2005, which designated the U.S. and claims benefit of FR 0413136, filed 9 Dec. 2004, the entire contents of each of which are hereby incorporated by reference.

The invention concerns compositions and methods for treating ocular pathologies, in particular ocular surface pathologies in mammals, particularly humans or animals. The invention more specifically concerns compositions and methods enabling the regulation of paracellular permeability of the ocular surface epithelium, corresponding to the anterior segment of the eye. The compositions and methods of the invention are based in particular on the use of agents or conditions modulating cytoskeletal tension of the epithelial cells of the conjunctiva and cornea. The invention can be used for preventive or curative treatment of ocular pathologies such as pathologies caused by an allergy (allergic conjunctivitis for example) or inflammation, infectious conjunctivitis, various keratitis and dry eye syndrome.

At the anterior segment of the eye, the corneal and conjunctival epithelia are non-keratinized and of the stratified type. They protect the eye against external aggressions, the ocular surface being a transitional mucosa between the deep ocular medium and the external environment. Said epithelium is an anatomic and functional barrier which, by virtue of its structure and the quality of the interface with the lacrimal film, protects the components of the conjunctiva and cornea as well as the intraocular medium. Said epithelium is a competitive barrier between fluid loss and penetration of pathogens. It also protects the eye from any abrasion. For said barrier to be efficient, the cells constituting the epithelium must adhere tightly to each other. They must also adhere to subjacent cellular components (Apostol S. and Carstocea B., Oftalmologia 1994; 38(2): 101-6). Considering the vulnerable position of the epithelium at the external surface of the eye, the response of the epithelium to any aggression must be rapid and efficient.

The inventors have discovered that the resistance of the aforementioned ocular epithelial barrier is associated with the permeability of said epithelium. The ocular epithelium is the unique site of exchange between the external medium of the eye (composed mainly of tears) and the internal medium. These exchanges can take place either across the cells of the epithelium, or through parallel networks. Thus, at the level of the ocular mucosa, water and electrolyte transport, or else absorption of small molecules (molecular weight generally less than approximately 1000 Da), take place by a transcellular route, i.e., across epithelial cells. On the other hand, absorption of large molecules and the passage of antigens and/or toxins occur principally by the paracellular route, at the level of "tight junctions" located between epithelial cells [(Gobbels M. et al., Fortschr. Ophtamol 1990; 87 (6): 646-8), (Noske W. et al., Arch Clin Exp Ophtalmol 1994; 232 (110): 608-13), (Sugrue S. P. and Zieske J. D., Exp Eye Res 1997; 64: 11-20), (Hamalunem M. et al., Ophtalmol Vis Sci 1997; 38 (36): 27-34)].

Epithelial tight junctions (TJ) are structures which link the cells lining mucosal epithelia. At the eye, said structures ensure and control paracellular transepithelial transport of the lacrimal film and of various macromolecules (allergens, irritants, toxins, microorganisms, etc.) towards the tissues of the eye. These flexible structures, attached to the cytoskeletal components composed of actin and myosin filaments (Turner J. R. et al., Am J Physiol 1997; 273 (4Pt): C1378-85), are formed by the association of transmembrane proteins (occludins, claudins) and cytoplasmic proteins (zona occludens proteins ZO-1, ZO-2, cingulins), (Sugrue S. P. and Zieske J. D., Exp Eye Res 1997; 64:11-20), (Yi X. et al., Ophtalmol Sci Res 2000; 41 (13): 4093-100)]. As a result, the epithelium of the ocular surface, by virtue of its anatomic structure and the quality of its interface with the lacrimal film whose action is to continuously drain and eliminate microorganisms, foreign bodies and desquamated epithelial cells, provides a barrier function necessary for the protection of the subjacent cellular components and intraocular medium.

Some aggressive agents can however disrupt the stability of this ocular barrier, inducing alterations in transepithelial permeability related to modifications of paracellular permeability. An increased permeability promotes greater penetration of certain allergens, pathogens and chemical molecules towards the underlying cells.

By releasing oxygen free radicals, oxidative stress plays an important role in the genesis of pathologies affecting the ocular surface. Free radicals are highly reactive, toxic chemical species which alter epithelial cell membranes. The superoxide anion formed from molecular oxygen reacts with hydrogen peroxide to form the hydroxyl radical. The latter in turn reacts with membrane polyunsaturated fatty acids thereby inducing the formation of highly aggressive lipid peroxides, which are responsible for major disruptions of the membrane [Fridovitch I., Science 1978; 201 (4359): 875-80]. In vitro studies show that vitamin A deficiency can lead to an alteration of permeability with reduction of paracellular permeability to $^3$H-mannitol, keratinization of the conjunctival epithelium (Huang A. J. et al., Invest Ophtalmol Vis Sci 1991; 31 (3): 429-35) and loss of caliciform cells.

In the case of ocular dryness, different factors can be responsible for an alteration of the epithelium. These ocular disorders can be caused by exposure to radiation (ultraviolet A and B, X rays, photorefractive surgery), bacteria, viruses, fungi, allergens, contact lens wear (Mc Namara N. A. et al., Br J Ophtamol 1998; 82 (4): 376-81). They can be genetic in origin such as in Gougerot-Sjogren syndrome.

Alterations of paracellular permeability in the cornea have also been demonstrated. They are linked to acute or chronic dehydration of the ocular surface [(Lofebalo L. et al., Int J Immunopathol Pharmacol 1999; 12 (3): 133-7), (Kabuyonna I. and Arakawa T. J., Ocul Pharmacol Ther 2003; 19 (3): 281-9)].

The permeability of the ocular surface epithelium, as shown by the use of horse radish peroxidase (HRP), can be altered by preservatives which are present in eye drops or antiseptic substances such as quaternary ammonium salts. Benzalkonium chloride (BAC or BAK), an ingredient of all multidose eye drop formulations such as those used in glaucoma treatment, causes lysis of cell membranes at the ocular surface, even at very low doses (Tonjum A. M., Acta Ophtalmol (Copenh) 1975; 53(3): 335-47), and alterations of paracellular permeability.

In addition, alterations of both conjunctival and corneal permeability can occur after trauma to the ocular surface, during the healing phases. Thus, biopsy was found to induce an increase in paracellular permeability, correlated with the status of the epithelium (Huang A. J. et al., Invest Ophtamol Vis Sci 1990; 32 (3): 633-39).

Consequently, the alteration of epithelial tight junctions at the ocular surface can lead to sensitization, since certain allergens, pathogens and/or chemical molecules can cross said epithelium to interact with immune cells of the eye. The conditions in which said transfer is possible have been poorly documented in vitro and so far there is no evidence for the involvement of said junctions in vivo in the development of sensitization. Nevertheless it is known that the increased presence of microorganisms, allergens and/or chemical molecules is responsible for allergic and inflammatory phenomena, often accompanied by pain leading to a chronic pathology.

The invention results from the demonstration in vivo of the role of epithelial tight junctions in ocular pathologies, in particular pathologies affecting the ocular surface. The opening of tight junctions induced by an allergic reaction to instillation of a mast cell degranulation agent (product 48/80: condensate of N-methyl-p-methoxyphenethylamine and formaldehyde) or an irritant chemical such as benzalkonium chloride, modifies paracellular permeability of the ocular epithelium. The invention proposes, for the first time, a therapeutic approach to ocular pathologies, in particular ocular surface pathologies, based on the use of compounds or conditions enabling modulation of cytoskeletal tension of said ocular epithelial cells. Thus, said compounds or conditions allow modulation of cytoskeletal tension of ocular epithelial cells or direct regulation, preferably reduction, even blockage, of the opening of tight junctions of the ocular epithelium. In particular said approach makes it possible to control the opening or closing of ocular epithelium tight junctions, without necessarily having to resort to de novo protein synthesis and/or important protein and/or structural degradations in the epithelium. The invention enables a regulation of ocular surface epithelial permeability which is specific, fine and reactive, and hence an action on the passage of allergens, pathogens and/or chemical molecules towards immune cells. The inventive compositions and methods are particularly well adapted to obtaining a rapid biological effect which can be controlled over time (reversible).

Polynuclear neutrophil infiltration into the aqueous humor following application of a mast cell degranulation agent, product 48/80, on the cornea, is characterized by an infiltration of polynuclear neutrophil cells as described in the literature (Allansmith et al., Acta Ophtalmol. 1989; 192: 145-153S). The inventors have shown that infiltration is associated with an increase in the activity of myeloperoxidase (MPO), an enzyme released by activated neutrophils, and that said increase could be prevented by pretreatment with ML-7, an inhibitor of epithelial cell cytoskeletal contraction, which acts by inhibiting the action of the kinase catalyzing phosphorylation of myosin light chains. This effect corresponds to a reduction of cytoskeletal tension in corneal epithelial cells induced by inflammation and results in suppression of said inflammation related to neutrophil accumulation in the aqueous humor.

In a second series of experiments, the inventors have further shown that corneal irritation produced by instillation of benzalkonium chloride solution for 10 minutes followed by rinsing, led to an increase in MPO in the eye. The latter, which was very high even after 6 hours, was also suppressed by pretreatment with ML-7 administered by the intraperitoneal route.

In these experiments, then, it appears that ML-7 can prevent inflammation by blocking the ocular penetration of aggressive agents (P48/80 and benzalkonium chloride).

A first object of the invention relates more particularly to the use of a compound modulating the tension of the cytoskeleton of ocular epithelial cells, in particular of ocular surface epithelial cells, for preparing a medicament for preventive or curative treatment of ocular surface pathologies in humans or animals.

Another object of the invention relates to a pharmaceutical composition comprising at least one compound modulating the tension of the cytoskeleton (in particular modulating the opening of tight junctions) of ocular surface epithelial cells and a pharmaceutically acceptable excipient, said composition being formulated for local administration (via for example eye drops, a gel, etc., to be directly applied on the eye).

The invention also relates to a method for preventive or curative treatment of ocular pathologies, in particular pathologies of the ocular surface, comprising administering to a mammal, in particular a human subject or an animal, an effective amount of a compound modulating the tension of the cytoskeleton of ocular epithelial cells.

The invention is based on the use of compounds modulating (preferably inhibiting) the tension and state of contraction of the cytoskeleton of ocular epithelial cells, in particular ocular epithelial cells of the anterior segment of the eye. As indicated earlier, this approach makes it possible to control the opening and closing of ocular epithelium tight junctions without necessarily having to resort to de novo protein synthesis and/or important protein and/or structural degradations in the epithelium.

The proteins composing tight junctions are associated with the cytoskeleton of the cells they link together. The invention allows the modulation of the tension of the cytoskeleton in subjects with ocular diseases or disorders so as to act in a non-destructive and transient manner on the permeability of the ocular epithelium. Thus, contraction of the cytoskeleton promotes opening of tight junctions, while relaxation of the cytoskeleton (or inhibition of contraction) promotes closing of said junctions.

Preferably, then, compounds that modulate the contraction of the cytoskeleton of ocular epithelial cells are used in the invention. Depending on the condition to be treated, compounds are used which inhibit contraction of the cytoskeleton of ocular epithelial cells, or in contrast which activate or promote it.

The activity of the compound on the tension of the cytoskeleton can be direct or indirect, that is to say, directed on the very components of the cytoskeleton, or on regulators of its tension. Compounds acting directly on the tension of the cytoskeleton are preferred. Compounds displaying selective activity on the tension of the cytoskeleton, that is to say, typically, compounds which do not directly affect the structure of the proteins composing the tight junctions, are particularly preferred.

According to the invention, a compound is considered to modulate the tension of the cytoskeleton when it modulates the opening of tight junctions. An inhibitory effect on the contraction or tension of actin and/or myosin filaments does not necessarily have to be complete or total. It suffices that it reduces the contraction or tension of the cytoskeleton enough to reduce the opening of tight junctions. This reduction corresponds to a reduction of at least 25%, preferably approximately 30%, even more preferably approximately 50% of the paracellular permeability of the ocular epithelium.

Different types of compounds may be used within the scope of the invention. Thus, according to the invention, the term "compound" must be understood in a broad sense, that is to say, as denoting any agent, substance, composition, condition, treatment or method enabling modulation of the tension of the cytoskeleton. Advantageously, it is an agent (e.g., a molecule) or a combination or association of agents.

According to a first preferred embodiment, one uses compounds which inhibit (or modulate) the contraction or tension of myosin and/or actin light chains, or compounds which inhibit (or modulate) the degradation of actin.

Examples of such compounds include in particular inhibitors of myosin light chain kinase (MLCK).

A particular example of selective MLCK inhibitor is the compound ML-7 {1-(5-iodonaphthalene-1-sulfonyl)-1H-hexahydro-1,4-diazepine} (Makishima M. et al., Feb Lett 1991; 287: 175). Other particular examples of such inhibitors are in particular the compound ML-9 (Wilson D. P. et al., 2001) and other nonselective compounds such as wortmannin (Warashina A., Life Sci 2000; 13: 2587-93), H-7 (Piao Z. F. et al., Mol Cell Biol Res Commun 2001; 4: 307-12) and KT 7692 (Warashina A., Life Sci 2000; 13: 2597-93).

Other targets acting on the tension of the cytoskeleton are in particular the myosin binding proteins, such as for example cingulin, or the junction molecules, such as cadherin-E, catenin-alpha or desmosomes. Modulation of the activity or expression of these proteins allows regulation of cytoskeletal tension, in the scope of the invention.

A particular object of the invention is therefore the use of a modulator (particularly an inhibitor) of the activity or expression of cytoskeleton molecules. For example the compound may be an antisense nucleic acid, a synthetic molecule, an antibody fragment, among others.

According to another embodiment, it is possible to use compounds that inhibit the synthesis of proteins or other molecules ensuring the binding between the proteins of the cytoskeleton and the proteins of tight junctions. Among proteins of tight junctions, particular examples include the occludins, claudins, ZO-1 and ZO-2. The invention discloses a means of modulating the opening or closing of tight junctions which is therefore based on regulating the synthesis of binding proteins between the cytoskeleton and the proteins of tight junctions. By stimulating said synthesis, the links between tight junctions and the cytoskeleton are expected to be strengthened, leading to lower permeability of the epithelium.

Other compounds that can be used in the invention are for example inhibitors of mitogen activated kinases (MAPKK), particularly MEK1 kinase or PI3-kinase, such as the compounds PD098,059 {2-(amino-3-methoxyphenyl)-4H-1-benzopyran-4-one} (Alessai et al., J Biol Chem 1995; 270: 27589) or LY294002 {2-(4-morpholinyl)-8-phenyl-1(4H)-benzopyran-4-one} (Vlahos et al., J Biol Chem, 1994; 269: 5241).

Other molecules that can be used to indirectly regulate the tension of the cytoskeleton are growth factors, such as endothelial growth factor (EGF) or certain cytokines which can be released by immune cells, such as interleukins-1, -4, -13, or factors such as IGF-1 or interferon gamma.

Another approach by which to indirectly regulate the tension of the cytoskeleton is based on the use of the GLP2 peptide ("glucagon-like peptide 2") or derivatives thereof, which can modify ocular epithelium permeability by an indirect effect on cytoskeletal contraction. Likewise, some molecules acting on receptors located at the apical pole of epithelial cells (e.g., proteinase receptors, PAR-2) can act indirectly on the cytoskeleton.

A preferred embodiment of the invention comprises the use of agents acting directly on the tension of the cytoskeleton, particularly molecules inhibiting cytoskeletal contraction, in particular molecules inhibiting the contraction or tension of myosin and/or actin light chains, or inhibiting actin degradation.

As indicated hereinabove, the compounds used are advantageously molecules, which may be alone or in combination of biological extracts, and the like. Said molecules may be synthetic, semisynthetic or biological, particularly of animal, viral, plant or bacterial origin.

The invention may be used for treating or managing ocular pathologies or disorders, in particular ocular surface disorders.

In particular, the invention relates to the use of a compound such as described hereinabove modulating the tension of the cytoskeleton of ocular epithelial cells for preparing a medicament for controlling (preferably for reducing) paracellular permeability of the ocular epithelium in subjects with ocular pathologies, in particular ocular surface pathologies.

The aforementioned uses of the invention are particularly efficacious in the treatment of an ocular pathology selected in the group consisting of keratitis, conjunctivitis, dry eye syndrome and any other alteration of paracellular permeability of the ocular epithelium. Situations which can cause such alterations can be, for example, contact lens wear or else the healing phases in a subject who has a trauma or a surgical wound to the ocular epithelium.

In particular, the invention is particularly adapted to the preventive or curative treatment of allergen sensitization. Allergy of the anterior segment of the eye is a common ocular pathology affecting 20% of the North American and European populations. The number of patients afflicted with this type of allergy is rising incessantly due to environmental factors and/or longer lifespan. At the cornea of the eye, said allergy is responsible for allergic keratitis. At the conjunctiva, the allergy causes conjunctivitis which manifests as red eye. There are several types of allergic conjunctivitis: seasonal conjunctivitis, environmental conjunctivitis, conjunctivitis caused by wearing contact lenses (giant papillary conjunctivitis) such as mentioned earlier, atopic conjunctivitis and conjunctivitis arising from the use of cosmetic products.

The inflammation produced by free radicals, which are often released under the effect of environmental factors (pollution, air conditioning, chemical agents, among others), affects the cornea and conjunctiva. This is the case in vernal conjunctivitis, a very widespread type in children and young adults. Atopic keratoconjunctivitis is another type which occurs in older patients who suffer from skin rashes. This type of nonseasonal conjunctivitis can cause severe damage to the cornea and conjunctiva if left untreated.

The invention can be used for the treatment or management of ocular pathologies caused by microorganisms, such as bacterial conjunctivitis (keratitis is a common complication of this type of conjunctivitis) and viral conjunctivitis (adenovirus), very often bilateral (and also usually associated with keratitis), with severe photophobia, pain and redness.

The invention can also be used for preventive or curative treatment or management of dry eye with a strong immuno-inflammatory component. More than 10 million people in the USA (representing 15% of the population over 65 years of age) suffer from this aggression to the ocular surface.

In this pathology, two types of syndromes may be distinguished:
  simple dry eye syndromes which are caused by environmental factors (pollution, radiation, air conditioning, contact lenses, computer screens, etc.), exacerbated by age, menopause and certain treatments.
  more serious forms which are often associated with genetic factors such as Gougerot-Sjogren syndrome. These forms lead to chronic, highly incapacitating disease and in the most severe cases can result in blindness.

Chronic inflammation is always omnipresent in the eye; it can be primary as in Gougerot-Sjogren syndrome, or secondary as in dry keratitis.

The invention can be used to prevent or treat any inflammation of the ocular surface in subjects exposed to preservatives (antiseptic substances), in particular in subjects presenting signs of intolerance related to clinical or subclinical inflammation induced by such an exposure. The most well-known preservatives on the market are the quaternary ammonium salts such as benzalkonium chloride (BAC) which is an ingredient of multidose eye drops such as those approved for the treatment of glaucoma. Said preservatives, by inducing free radical release and apoptosis of ocular cells, reach the corneal epithelium and stimulate infiltration of inflammatory cells into the conjunctiva.

Another particular object of the invention is the use of a compound such as defined hereinabove, for preparing a medicament for reducing, in a patient, the passage of a molecule known to have an inflammatory effect such as a preservative of multidose eye drops (preferably used in the treatment of glaucoma).

The invention can be used preventively in subjects presenting predispositions or susceptibility to the aforementioned disorders, or curatively at the time of pathological events either acute or chronic. The inventive compositions make it possible to attenuate the subjects' symptoms, in particular their suffering, and/or the cause of said disorders.

Another particular object of the invention thus relates to the use of a compound such as defined hereinabove, for preparing a medicament for reducing paracellular permeability of the ocular epithelium in subjects with acute or chronic inflammatory ocular diseases.

The invention is useful in a preventive and/or curative manner for example in elderly subjects for whom paracellular permeability is increased (Nzekwe E. U. and Maurice D. M., J Ocul Pharmacol 1994; 10(3): 521-3).

The invention shows in a surprising manner that suppressing the increase in paracellular permeability associated with opening of tight junctions prevents the development of ocular disorders, in particular ocular surface disorders.

A particular object of the invention is based on the use of a compound such as defined hereinabove, for preparing a medicament intended particularly to reduce paracellular permeability and sensitization to allergens, pathogens and/or chemical molecules, in subjects afflicted with or susceptible to ocular allergies.

The invention also relates to methods for preventing or treating the pathological conditions indicated earlier, comprising administering to a subject with an ocular pathology or susceptible to such pathologies, a compound or treatment such as defined hereinabove. Preferably, the compound or treatment is administered at an effective dose to reduce paracellular permeability of the ocular surface epithelium and/or to reduce sensitivity to pain and/or to reduce transepithelial migration of allergens towards corneal or conjunctival tissues.

The compound may be administered by different routes and in different forms. For instance, the compound may be in liquid or solid form, typically in the form of eye drops, gel, suppository, a solution for injection or an oral solution, etc. Compounds formulated for local administration (eye drops or gel for example.) or else for oral administration (oral solutions, tablets, ampuls, etc.) are preferred. Of course, other formulations are possible, such as injections (intravenous, intraperitoneal, intradermal, subcutaneous, intramuscular, intraarterial, etc.).

The compounds such as defined herein may be used alone, in combination and/or in association with at least one other active agent, such as for example other active substances used in the treatment of ocular pathologies, in particular ocular surface pathologies. Examples are artificial tears, certain antioxidants, different forms of cyclosporine, antiseptic, antibiotic or antiviral agents, etc. These different agents may be used in combination therapy, administered separately, in combination, spread out over time or concomitantly.

Thus a particular object of the invention is the use of a compound such as described hereinabove, in combination with an antiseptic, antibiotic or antiviral composition, for preparing a medicament for reducing paracellular permeability of the ocular epithelium in a subject with an ocular pathology caused by the penetration of microorganisms, such as bacterial and/or viral keratitis.

Another object of the invention relates to a pharmaceutical composition comprising at least one compound modulating the tension of the cytoskeleton (in particular the opening of tight junctions) of ocular epithelial cells, in particular ocular surface epithelial cells, and a pharmaceutically acceptable excipient, said composition being formulated for local administration (eye drops or gel, for example). Preferably, the composition is in the form of eye drops and/or gel. Excipients suitable for the gel or eye drop formulation can be selected in the group consisting of water for injections, sodium hydroxide, glycerol, hypromellose, polyvinyl alcohol, sorbitol, potassium gluconate, distilled water, sodium chloride, sodium borate, boric acid, citric acid, dibasic sodium phosphate, methylhydroxypropylcellulose, polysorbate 20, sodium metabisulfite, sodium edetate, methyl parahydroxybenzoate, benzalkonium chloride, vaseline oil and chlorbutanol. Preferably, the excipient is selected from among glycerol, benzalkonium chloride, sodium hydroxide and water for injections.

The quantity of compound modulating the tension of the cytoskeleton (in particular the opening of tight junctions) of ocular epithelial cells in the inventive composition varies over a wide range and in particular according to the nature of the compound chosen, the condition of the subject to be treated, the pathology to be treated and/or the desired effect. Thus, one skilled in the art is able to determine the efficacious quantity of the modulator compound of the tension of the cytoskeleton of ocular epithelial cell (in particular tight junction opening) in the composition and/or for the treatment according to the invention.

Other aspects and advantages of the invention will become apparent in the following examples, which are given for purposes of illustration and not by way of limitation.

LEGENDS OF FIGURES

FIG. 1: Experimental protocol for example 1. Animals received two pretreatments with ML-7 [1 mg/kg by the intraperitoneal (IP) route] on the day before instillation of P48/80 (in the morning and evening) and one pretreatment two hours before instillation.

Figure 2:
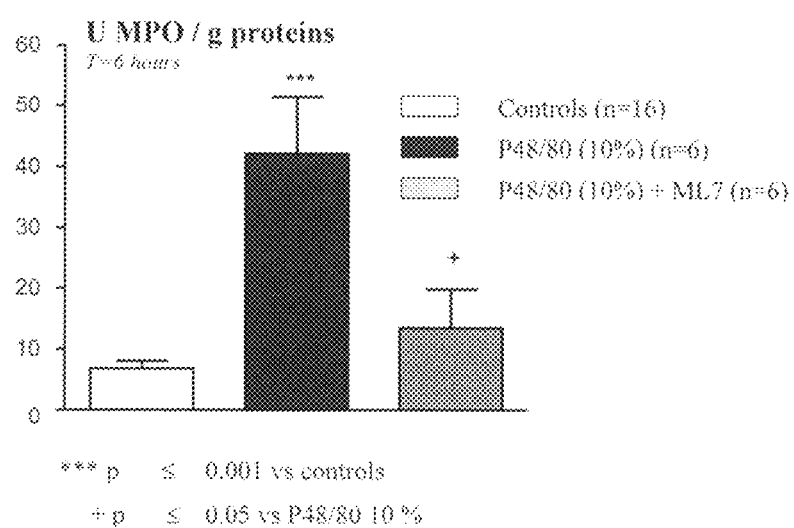

FIG. 2: MPO (myeloperoxidase) activity in the eye and effect of P48/80 and ML-7. In baseline conditions, MPO activity in the eye was low (8.5±1.2 U/g.protein) and the values did not differ between the two eyes. Treatment of the left eye with P48/80 led to a sharp 407% increase in MPO activity (43.1±11.3 U/g.protein) corresponding to neutrophil accumulation. This increase was inhibited by ML-7.

Figure 3:
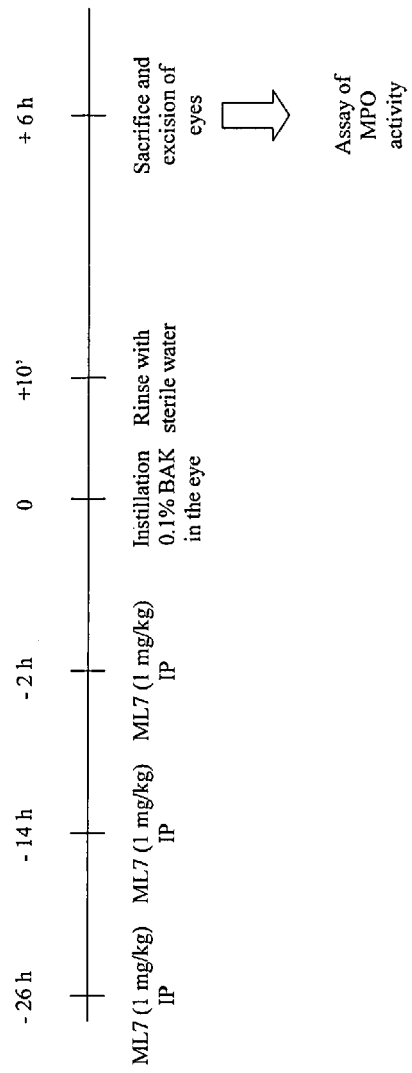

FIG. 3: Experimental protocol for example 2. Animals received two pretreatments with ML-7 [1 mg/kg given by the intraperitoneal (IP) route] on the day before instillation of 0.1% BAK (in the morning and evening) and one pretreatment two hours before instillation. They were sacrificed six hours after rinsing and the eyes were excised in order to assay MPO activity.

Figure 4:
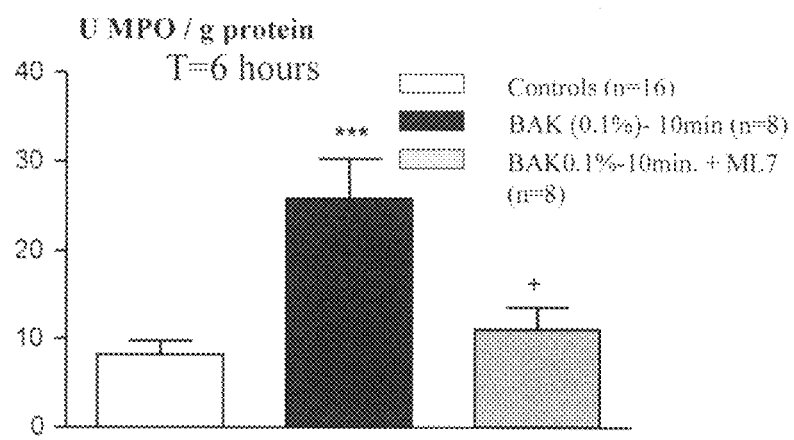

FIG. 4: MPO (myeloperoxidase) activity in the eye and effect of benzalkonium chloride and ML-7. In baseline conditions, MPO activity in the eye was 8.2±1.9 U/g.protein.

Application of 0.1% benzalkonium chloride led, after six hours, to a very sharp increase (321%) of total MPO activity in the eye (26.4±7.2 U/g.protein). This increase was inhibited by pretreatment with ML-7 administered by the IP route.

Figure 5:
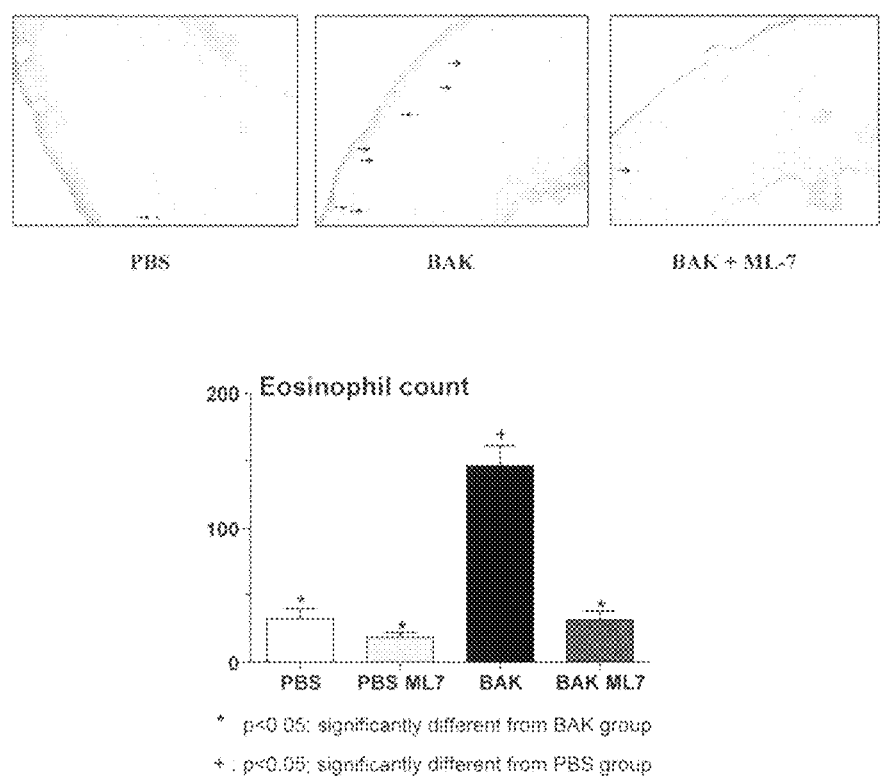

FIG. 5: Effect of ML-7 on polynuclear eosinophil accumulation at the corneo-conjunctival junction induced by ML-7. Infiltration of polynuclear eosinophils induced by instillation of 10 μL of BAK. After six hours, the increase in eosinophils was highly significant. This increase was inhibited by local administration of ML-7.
Upper panel: histological images after Direct Red staining.
Lower panel: eosinophil count in venous plexus of sclera, density per square mm (means±SD; n=8)

Figure 6:
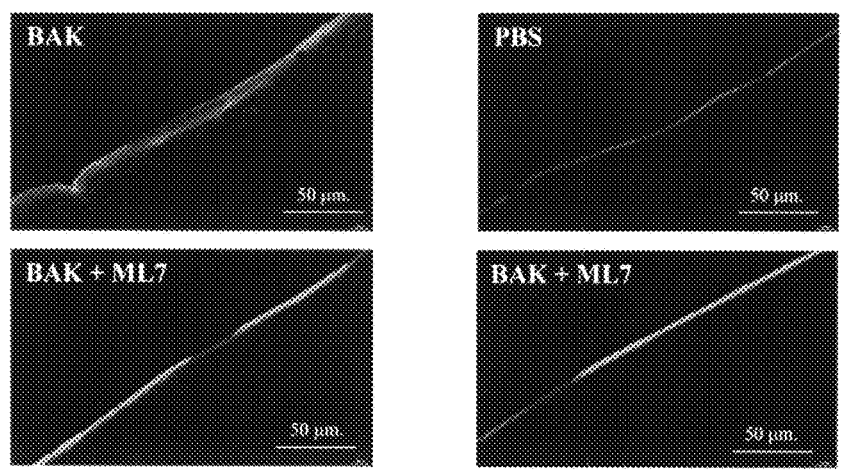

FIG. 6: Comparative effect of benzalkonium chloride (BAK), PBS (solvent) and BAK+local pretreatment with ML-7 on the extent of fluorochrome penetration through rat cornea.
Images obtained by fluorescence of the external corneal surface in the rat after ex vivo avidin-fluorescein biotinylation of the whole eye by avidin-fluorescein following cryosection (6 μm) (external side of cornea facing up)

EXAMPLES

Example 1

Effects of an MLCK Inhibitor (ML-7) Administered Systemically (IP) on Ocular Inflammation Induced by Corneal Instillation of a Mast Cell Degranulation Product The corneal irritation model which was used has been validated in the rat (Allansmith et al., Acta Ophtalmol, 1989; 192S: 145-153) and in the rabbit (Bucolo et al., J. Ocul. Pharmacol, 1993; 9: 321-332).
a) Materials and Methods
Animals: Three groups of eight male Wistar rats (200-250 g) housed in individual cages were used. Animals were given a standard diet (UAR, Villemoisson, Epinay sur Orge) and drinking water ad libitum.
Inflammation induction: Inflammation was induced by instillation in the eye of 10 μl of a 10% P48/80 solution (0.1 g/ml). The control eye was instilled with 10 μl of 1×PBS.
Assay of myeloperoxidase activity: The eyes were excised and homogenized in phosphate buffer with the aid of a polytron. They were then subjected to three freeze/thaw cycles (liquid nitrogen/37° C. water bath). After centrifugation at 10,000 rpm for 15 min at 4° C., the pellets were resuspended in HTAB buffer and sonicated for 10 sec. After a second centrifugation, MPO activity was assayed from the supernatant in a reaction buffer containing O-dianisidine hydrochloride and 0.0005% hydrogen peroxide. The change in absorbance at 460 nm was measured on a spectrophotometer.
Experimental protocol: Animals received two pretreatments with ML-7 (1 mg/kg IP) on the day before instillation of P48/80 (morning and evening) and one pretreatment two hours before instillation.
They were sacrificed six hours after instillation and the eyes were excised in order to assay total myeloperoxidase (MPO) activity in the whole eye (FIG. 1).
b) Results (FIG. 2)
In baseline conditions, MPO activity in the eye was low (8.5±1.2 U/g.protein) and the values did not differ between the two eyes. Treatment of the left eye with P48/80 led to a sharp 407% increase in MPO activity (43.1±11.3 U/g.protein) corresponding to the accumulation of neutrophils. This increase was inhibited by ML-7.

Example 2

Effects of an MLCK Inhibitor (ML-7) on Ocular Inflammation (Neutrophil Infiltration) Induced by Corneal Instillation of benzalkonium chloride The benzalkonium salt (BAK) corneal irritation model has been widely used in both in vitro and in vivo studies. The protocol is based on an in vitro study (Xu et al., 2000) adapted to in vivo conditions in the rat after preliminary tests to adjust times and concentrations.
a) Materials and Methods
Animals: Male Wistar rats (200-250 g) housed in individual cages were used. Animals were given a standard diet (UAR, Villemoisson, Epinay sur Orge) and drinking water ad libitum.
Inflammation induction: Inflammation was induced by instillation in the eye of 10 μl of 0.1% BAK solution (1 mg/ml). The control eye was instilled with 10 μl of 1×PBS. Ten minutes after instillation, the eyes were rinsed with 1 ml of sterile water.
Assay of myeloperoxidase activity: The eyes were excised and homogenized in phosphate buffer with the aid of a polytron. They were then subjected to three freeze/thaw cycles (liquid nitrogen/37° C. water bath). After centrifugation at 10,000 rpm for 15 min at 4° C., the pellets were resuspended in HTAB buffer and sonicated for 10 sec. After a second centrifugation, MPO activity was assayed in the supernatant in a reaction buffer containing O-dianisidine hydrochloride and 0.0005% hydrogen peroxide. The change in absorbance at 460 nm was measured on a spectrophotometer.
Experimental protocol: Animals received two pretreatments with ML-7 (1 mg/kg IP) on the day before instillation of 0.1% BAK (morning and evening) and one pretreatment two hours before instillation. They were sacrificed six hours after rinsing and the eyes were excised in order to assay total myeloperoxidase (MPO) activity (FIG. 3).
b) Results (FIG. 4)
In baseline conditions, MPO activity in the eyes was 8.2±1.9 U/g.proteins. Instillation of 0.1% benzalkonium chloride led, after six hours, to a very sharp 321% increase in total MPO activity in the eye (26.4±7.2 U/g.protein). This increase was inhibited by pretreatment with ML-7 administered by the IP route.

Example 3

Effects of Local Application of ML-7 on Eosinophil Infiltration and Tight Junction Permeability Induced by Benzalkonium Chloride (BAK), at the Eyes of Rats a) Materials and Methods
Animals: Four groups of male Wistar rats (Janvier, Le Genest St Isle, France), weighing 300-350 g were used: BAK+sodium carmellose, BAK+ML-7, PBS+sodium carmellose, PBS+ML-7; PBS and sodium carmellose being the solvents for benzalkonium (BAK) and ML-7, respectively.
ML-7 pretreatment: Animals received a local application of ML-7 (Sigma, France) 24 hours, 12 hours and 30 minutes before chemical induction of ocular inflammation. Thus, each eye was treated with 100 μg of ML-7 in 10 μl of eye drops (sodium carmellose 4 mg/0.4 ml) or with 10 μl of eye drops alone.

Inflammation induction: Thirty minutes after the third application of ML-7 or the eye drops alone, each eye was treated with 10 µl of 0.5% benzalkonium chloride (Sigma-Aldrich, Steinheim, Germany) in PBS or 10 µl of PBS alone. After 10 minutes, the eyes of all the rats were rinsed with 250 µl of sterile water.

Eye excision: Six hours after application of benzalkonium chloride or PBS, the animals were anesthetized with pentobarbital (80 mg/kg IP) (Ceva Santé Animale, Libourne, France), sacrificed by decapitation and the eyes were immediately excised to be frozen directly or after surface biotinylation (tight junction permeability test).

Measurement of polynuclear eosinophil infiltration: Polynuclear eosinophil leukocytes were specifically stained with Direct Red and counted in the venous plexus region of the sclera. Immediately after excision, the eyes were embedded in protective tissue freezing medium (Tissue Tek® OCT compound, Sakura Finetek, Inc., CA, USA), frozen in liquid nitrogen and stored at −80° C. Six micrometer thick slices were prepared with a cryostat and fixed in cold acetone for 10 minutes. After drying, the slices were hydrated by successive baths in toluene (5, 3 and 2 minutes), then 100% ethanol (3 and 2 minutes), 95% ethanol (3 and 2 minutes) and 50% ethanol (2 minutes). The sections were then stained for 20 minutes in a solution of 0.03% Sirius red in 50% ethanol (Direct Red 75 dye content 30%, Sigma-Aldrich, Steinheim, Germany), rinsed in running water for 5 minutes, then mounted in an aqueous medium (glycerol/PBS, 50:50 V/V). Eosinophils, stained bright pink against a light background, were counted in the venous plexus region of the sclera under a Nikon Eclipse 90 i microscope equipped with a Nikon DXM1200F digital camera. The area of the zone to be counted was determined with Nikon Lucia image analysis software release 4.8 and counts were expressed as the number of eosinophils per mm$^2$. The results obtained for the four experimental groups were compared by a one-way analysis of variance, followed by a Bonferroni multiple comparison test with statistical significance set at $p<0.05$.

Measurement of tight junction permeability—Surface biotinylation: The permeability of tight junctions in the cornea was evaluated by biotinylation of surface proteins. The chosen biotinylation reagent is water-soluble and contains an aminocaproyl spacer group, which lowers steric hindrance during avidin coupling. Immediately after excision, the eyes were incubated for 30 minutes at room temperature with gentle stirring in a solution containing sodium biotinamidohexanecarboxylate and 3-sulfó-N-hydroxysuccinimide at 1 mg/mL, in PBS (Sigma-Aldrich, Steinheim, Germany). The eyes were then rinsed three times in PBS, embedded in protective tissue freezing medium (Tissue Tek® OCT compound, Sakura Finetek, Inc., CA, USA), frozen in liquid nitrogen and stored at −80° C. Six micrometer thick slices were prepared with a cryostat and fixed in cold acetone for 10 minutes. After drying, the slices were labelled for 30 minutes in the dark with avidin D-FITC (Vector Laboratories, Inc., Burlingame, Calif., USA) diluted 250-fold in PBS-Tween containing 1% BSA, then rinsed three times for 5 minutes in PBS-Tween, in the dark. The slides were then mounted in fluorescence medium (Cappel fluorostab embedding medium, MP Biomedicals, Inc., Aurora, Ohio, USA) and examined under a Nikon Eclipse 90 i fluorescence microscope equipped with a Nikon DXM1200F digital camera. The images were analyzed with Nikon Lucia image analysis software release 4.8. As no significant differences in corneal thickness were observed between the different experimental groups ($102\pm10$ µm, $110\pm9$ µm, $115\pm13$ µm and $124\pm8$ µm for BAK+sodium carmellose, BAK+ML-7, PBS+sodium carmellose and PBS+ML-7 groups, respectively), the depth of fluorescence labelling reflects the permeability of external corneal epithelial tight junctions to the biotinylation reagent.

b) Results (FIGS. 5 and 6)

a) Polynuclear Eosinophil Infiltration (FIG. 5)

Application of 10 µl of benzalkonium chloride in the eye led, after six hours, to a highly significant increase in the number of Direct Red stained polynuclear eosinophils in the venous plexus region of the sclera, which is evidence of severe ocular inflammation.

This polynuclear eosinophil infiltration was significantly inhibited after local application of ML-7.

c) Measure of Tight Junction Permeability (FIG. 6)

Application of 10 µl of benzalkonium chloride in the eye led, after six hours, to an opening of corneal epithelial tight junctions as manifested by deeper penetration of the fluorescent and by its diffusion. Pretreatment with ML-7 suppressed this increase in the diffusion and thickening of the fluorescent zone.

The invention claimed is:

1. A method for reducing paracellular permeability of the ocular epithelium in subjects exposed to at least one preservative agent comprising administering to a mammal in need of such treatment an effective amount of a selective MLCK (Myosin Light Chain Kinase) inhibitor, wherein the selective MLCK inhibitor is selected from the group consisting of {1-(5-iodonaphthalene-1-sulfonyl)-1H-hexahydro-1,4-diazepine} (ML-7) and 1-(5-chloronaphtalene-1-sulfonyl)homopiperazine-HCl (ML-9), and wherein the at least one preservative agent causes an increase in paracellular permeability of ocular epithelium.

2. The method according to claim 1, wherein the inhibitor is administered by the oral, local, intravenous or intraperitoneal route.

3. The method according to claim 1, wherein the preservative agent is benzalkonium chloride.

4. A method for reducing the ocular inflammation induced by a preservative agent, comprising administering to a mammal in need of such treatment an effective amount of a selective MLCK (Myosin Light Chain Kinase) inhibitor, wherein the selective MLCK inhibitor is selected in the group consisting of {1-(5-iodonaphthalene-1-sulfonyl)-1H-hexahydro-1,4-diazepine} (ML-7) and 1-(5-chloronaphtalene-1-sulfonyl)homopiperazine-HCl (ML-9), wherein the preservative agent causes an increase in paracellular permeability of the ocular epithelium.

5. The method of according to claim 4, wherein the preservative agent is benzalkonium chloride.

6. The method of claim 1, wherein said mammal is being treated for a surface ocular pathology selected from the group consisting of keratitis, conjunctivitis and dry eye syndrome.

7. The method of claim 4, wherein said mammal is being treated for a surface ocular pathology selected from the group consisting of keratitis, conjunctivitis and dry eye syndrome.

* * * * *